United States Patent
Barrett et al.

(10) Patent No.: US 7,169,816 B2
(45) Date of Patent: Jan. 30, 2007

(54) 4-BROMO OR 4-IODO PHENYLAMINO BENZHYDROXAMIC ACID DERIVATIVES AND THEIR USE AS MEK INHIBITORS

(75) Inventors: Stephen Douglas Barrett, Hartland, MI (US); Alexander James Bridges, Saline, MI (US); Annette Marian Doherty, Nr Canterbury (GB); David Thomas Dudley, Ann Arbor, MI (US); Alan Robert Saltiel, Ann Arbor, MI (US); Haile Tecle, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 11/249,543

(22) Filed: Oct. 12, 2005

(65) Prior Publication Data
US 2006/0052608 A1  Mar. 9, 2006

Related U.S. Application Data

(60) Continuation of application No. 10/967,427, filed on Oct. 18, 2004, now abandoned, which is a division of application No. 10/163,890, filed on Jun. 4, 2002, now Pat. No. 6,821,963, which is a continuation of application No. 09/462,239, filed as application No. PCT/US98/13106 on Jun. 24, 1998, now abandoned.

(60) Provisional application No. 60/051,440, filed on Jul. 1, 1997.

(51) Int. Cl.
*A61K 31/166* (2006.01)
*C07D 233/64* (2006.01)

(52) U.S. Cl. ..................... 514/615; 564/163
(58) Field of Classification Search ................ 514/615; 564/163
See application file for complete search history.

(56) References Cited

U.S. PATENT DOCUMENTS 5,155,110 A  10/1992  Connor et al.
5,525,625 A  6/1996  Bridges et al.
5,877,190 A  3/1999  Dhainaut et al.
6,251,943 B1 *  6/2001  Barrett et al. ............... 514/564

FOREIGN PATENT DOCUMENTS

EP  0316630  5/1989
WO  WO89/03818  5/1989
WO  WO98/37881  9/1998

OTHER PUBLICATIONS

Connor, D. et al., "Dual Inhibitors Of 5-Lipoxygenase And Cyclooxygenase," *Biological Inhibitors*, 1996, Harwood Academic Publishers, Netherlands, 2, 47-86.

\* cited by examiner

*Primary Examiner*—Joseph K. McKane
*Assistant Examiner*—Janet L. Coppins
(74) *Attorney, Agent, or Firm*—Bryan C. Zielinski; Galina M. Yakovleva

(57) ABSTRACT

Phenylamino benzhydroxamic acid derivatives of the formula

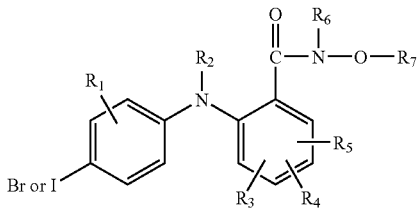

where $R_1$, $R_2$, $R_3$, $R_4$, $R_5$, and $R_6$ are hydrogen or substituent groups such as alkyl, and where $R_7$ is hydrogen or an organic radical, are potent inhibitors of MEK and, as such, are effective in treating cancer and other proliferative diseases such as psoriasis and restenosis.

16 Claims, No Drawings

4-BROMO OR 4-IODO PHENYLAMINO BENZHYDROXAMIC ACID DERIVATIVES AND THEIR USE AS MEK INHIBITORS

This application is a continuation application of U.S. Ser. No. 10/967,427 filed on Oct. 18, 2004, which is a divisional application of U.S. Ser. No. 10/163,890 filed on Jun. 4, 2002, now U.S. Pat. No. 6,821,963, which is a continuation application of U.S. Ser. No. 09/462,239 filed on Jan. 4, 2000, now abandoned, which is a 371 application of PCT/US98/13106 filed on Jun. 24, 1998, which claims the benefit of priority to U.S. Provisional Ser. No. 60/051,440 filed on Jul. 1, 1997, which are hereby incorporated by reference in their entireties.

FIELD OF THE INVENTION

This invention provides certain hydroxamic acid derivatives of anthranilic acids which inhibit certain dual specificity kinase enzymes involved in proliferative diseases such as cancer and restenosis.

BACKGROUND OF THE INVENTION

Proliferative diseases are caused by a defect in the intracellular signaling system, or the signal transduction mechanism of certain proteins. Cancer, for example, is commonly caused by a series of defects in these signaling proteins, resulting from a change either in their intrinsic activity or in their cellular concentrations. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, which is a G-protein that is activated when bound to GTP, and inactivated when bound to GDP.

The above mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras.GTP complex, are common in cancers, and lead to the signaling cascade below Ras being chronically activated.

Activated Ras leads in turn to the activation of a cascade of serine/threonine kinases. One of the groups of kinases known to require an active Ras.GTP for its own activation is the Raf family. These in turn activate MEK, which then activates MAP kinase. Activation of MAP kinase by mitogens appears to be essential for proliferation, and constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold, and it can now catalyze the phosphorylation of a large number of proteins, including several transcription factors and other kinases. Many of these MAP kinase phosphorylations are mitogenically activating for the target protein, whether it be another kinase, a transcription factor, or other cellular protein. MEK is also activated by several kinases other than Raf-1, including MEKK, and itself appears to be a signal integrating kinase. As far as is currently known, MEK is highly specific for the phosphorylation of MAP kinase. In fact, no substrate for MEK other than MAP kinase has been demonstrated to date, and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

This invention provides compounds which are highly specific inhibitors of the kinase activity of MEK. Both in enzyme assays and whole cells, the compounds inhibit the phosphorylation of MAP kinase by MEK, thus preventing the activation of MAP kinase in cells in which the Ras cascade has been activated. The results of this enzyme inhibition include a reversal of transformed phenotype of some cell types, as measured both by the ability of the transformed cells to grow in an anchorage-independent manner and by the ability of some transformed cell lines to proliferate independently of external mitogens.

The compounds provided by this invention are phenylamino benzhydroxamic acid derivatives in which the phenyl ring is substituted at the 4-position with bromo or iodo. U.S. Pat. No. 5,155,110 discloses a wide variety of fenamic acid derivatives, including certain phenylamino benzhydroxamic acid derivatives, as anti-inflammatory agents. The reference fails to describe the compound of this invention or their kinase inhibitory activity.

SUMMARY OF THE INVENTION

This invention provides 4-bromo and 4-iodo phenylamino benzhydroxamic acid derivatives which are kinase inhibitors and as such are useful for treating proliferative diseases such as cancer, psoriasis, and restenosis. The compounds are defined by Formula I

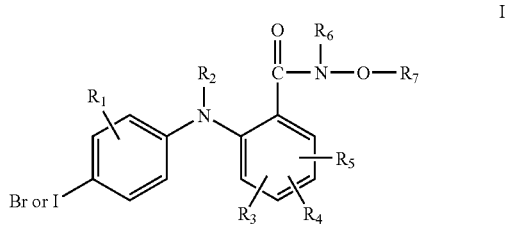

wherein:
$R_1$ is hydrogen, hydroxy, $C_1$–$C_8$ alkyl, $C_1$–$C_8$ alkoxy, halo, trifluoromethyl, or CN;
$R_2$ is hydrogen;
$R_3$, $R_4$, and $R_5$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—R$_9$, where R$_9$ is hydrogen, hydroxy, CO$_2$H or NR$_{10}$R$_{11}$;

n is 0 to 4;

m is 0 or 1;

R$_{10}$ and R$_{11}$ independently are hydrogen or C$_1$–C$_8$ alkyl, or taken together with the nitrogen to which they are attached can complete a 3- to 10-member cyclic ring optionally containing one, two, or three additional heteroatoms selected from O, S, NH, or N—C$_1$–C$_8$ alkyl;

R$_6$ is hydrogen, C$_1$–C$_8$ alkyl,

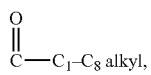

aryl, aralkyl, or C$_3$–C$_{10}$ cycloalkyl;

R$_7$ is hydrogen, C$_1$–C$_8$ alkyl, C$_2$–C$_8$ alkenyl, C$_2$–C$_8$ alkynyl, C$_3$–C$_{10}$ (cycloalky optionally containing a heteroatom selected from O, S, or NR$_9$); or R$_6$ and R$_7$ taken together with the N—O to which they are attached can complete a 5- to 10-membered cyclic ring, optionally containing one, two, or three additional heteroatoms selected from O, S, or NR$_{10}$R$_{11}$;

and wherein any of the foregoing alkyl, alkenyl, and alkynyl groups can be unsubstituted or substituted by cycloalkyl (or cycloalkyl optionally containing a heteroatom selected from O, S, or NR$_9$), aryl, aryloxy, heteroaryl, or heteroaryloxy.

Preferred compounds have Formula II

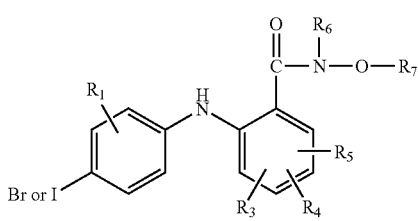

where R$_1$, R$_3$, R$_4$, R$_5$, R$_6$, and R$_7$ are as defined above. Especially preferred are compounds wherein R$_1$ is methyl or halo, and R$_3$, R$_4$, and R$_5$ are halo such as fluoro or bromo.

Another preferred group of compounds have Formula III

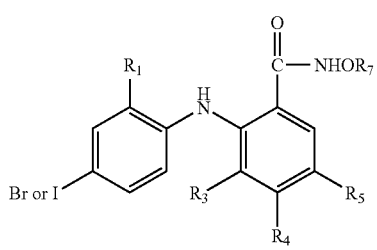

wherein R$_1$, R$_3$, R$_4$, R$_5$, and R$_7$ are as defined above.

The most preferred compounds are those wherein R$_1$ is methyl or halo such as F, Br, Cl, and I, R$_3$ is hydrogen or halo such as fluoro, R$_4$ is halo such as fluoro, and R$_5$ is hydrogen or halo such as fluoro or bromo. Such compounds have the formulas

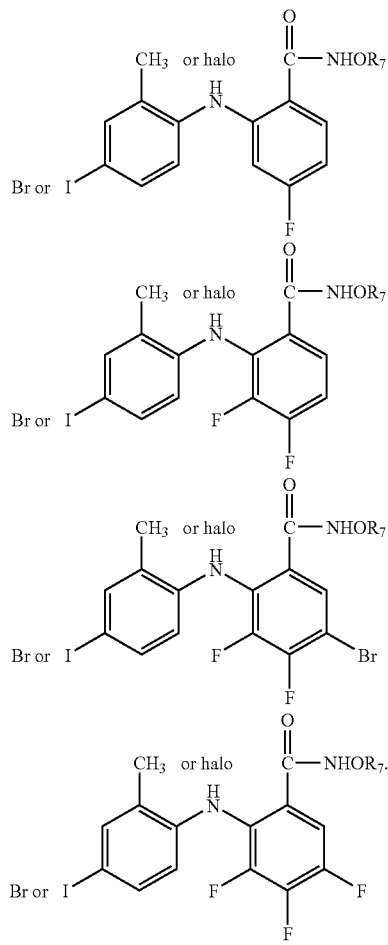

Specific compounds provided by the invention include the following:

3,4,5-Trifluoro-N-hydroxy-2-(4-iodo-2-methyl-phenylamino)-benzamide;

5-Chloro-3,4-difluoro-N-hydroxy-2-(4-iodo-2-methyl-phenylamino)-benzamide;

5-Bromo-3,4-difluoro-2-(2-fluoro-4-iodo-phenylamino)-N-hydroxy-benzamide;

N-Hydroxy-2-(4-iodo-2-methyl-phenylamino)-4-nitro-benzamide;

3,4,5-Trifluoro-2-(2-fluoro-4-iodo-phenylamino)-N-hydroxy-benzamide;

5-Chloro-3,4-difluoro-2-(2-fluoro-4-iodo-phenylamino)-N-hydroxy-benzamide;

5-Bromo-2-(2-chloro-4-iodo-phenylamino)-3,4-difluoro-N-hydroxy-benzamide;

2-(2-Fluoro-4-iodo-phenylamino)-N-hydroxy-4-nitro-benzamide;

2-(2-Chloro-4-iodo-phenylamino)-3,4,5-trifluoro-N-hydroxy-benzamide;

5-Chloro-2-(2-chloro-4-iodo-phenylamino)-3,4-difluoro-N-hydroxy-benzamide;

5-Bromo-2-(2-bromo-4-iodo-phenylamino)-3,4-difluoro-N-hydroxy-benzamide;

2-(2-Chloro-4-iodo-phenylamino)-N-hydroxy-4-methyl-benzamide;

2-(2-Bromo-4-iodo-phenylamino)-3,4,5-trifluoro-N-hydroxy-benzamide;

2-(2-Bromo-4-iodo-phenylamino)-5-chloro-3,4-difluoro-N-hydroxy-benzamide;
2-(2-Bromo-4-iodo-phenylamino)-N-hydroxy-4-nitro-benzamide;
4-Fluoro-2-(2-fluoro-4-iodo-phenylamino)-N-hydroxy-benzamide;
3,4-Difluoro-2-(2-fluoro-4-iodo-phenylamino)-N-hydroxy-benzamide;
2-(2-Chloro-4-iodo-phenylamino)-4-fluoro-N-hydroxy-benzamide;
2-(2-Chloro-4-iodo-phenylamino)-3,4-difluoro-N-hydroxy-benzamide;
2-(2-Bromo-4-iodo-phenylamino)-4-fluoro-N-hydroxy-benzamide;
2-(2-Bromo-4-iodo-phenylamino)-3,4-difluoro-N-hydroxy-benzamide;
N-Cyclopropylmethoxy-3,4,5-trifluoro-2-(4-iodo-2-methyl-phenylamino)-benzamide;
5-Chloro-N-cyclopropylmethoxy-3,4-difluoro-2-(4-iodo-2-methyl-phenylamino)-benzamide;
5-Bromo-N-cyclopropylmethoxy-3,4-difluoro-2-(2-fluoro-4-iodo-phenylamino)-benzamide;
N-Cyclopropylmethoxy-2-(4-iodo-2-methyl-phenylamino)-4-nitro-benzamide;
N-Cyclopropylmethoxy-3,4,5-trifluoro-2-(2-fluoro-4-iodo-phenylamino)-benzamide;
5-Chloro-N-cyclopropylmethoxy-3,4-difluoro-2-(2-fluoro-4-iodo-phenylamino)-benzamide;
5-Bromo-2-(2-chloro-4-iodo-phenylamino)-N-cyclopropylmethoxy-3,4-difluoro-benzamide;
N-Cyclopropylmethoxy-2-(2-fluoro-4-iodo-phenylamino)-4-nitro-benzamide;
2-(2-Chloro-4-iodo-phenylamino)-N-cyclopropylmethoxy-3,4,5-trifluoro-benzamide;
5-Chloro-2-(2-chloro-4-iodo-phenylamino)-N-cyclopropylmethoxy-3,4-difluoro-benzamide;
5-Bromo-2-(2-bromo-4-iodo-phenylamino)-N-ethoxy-3,4-difluoro-benzamide;
2-(2-Chloro-4-iodo-phenylamino)-N-ethoxy-4-nitro-benzamide;
2-(2-Bromo-4-iodo-phenylamino)-N-cyclopropylmethoxy-3,4,5-trifluoro-benzamide;
2-(2-Bromo-4-iodo-phenylamino)-5-chloro-N-cyclopropylmethoxy-3,4-difluoro-benzamide
2-(2-Bromo-4-iodo-phenylamino)-N-cyclopropylmethoxy-4-nitro-benzamide;
N-Cyclopropylmethoxy-4-fluoro-2-(2-fluoro-4-iodo-phenylamino)-benzamide;
N-Cyclopropylmethoxy-3,4-difluoro-2-(2-fluoro-4-iodo-phenylamino)-benzamide;
2-(2-Chloro-4-iodo-phenylamino)-N-cyclopropylmethoxy-4-fluoro-benzamide;
2-(2-Chloro-4-iodo-phenylamino)-N-cyclopropylmethoxy-3,4-difluoro-benzamide;
2-(2-Bromo-4-iodo-phenylamino)-N-cyclopropylmethoxy-4-fluoro-benzamide;
2-(2-Bromo-4-iodo-phenylamino)-N-cyclopropylmethoxy-3,4-difluoro-benzamide;
4-Fluoro-N-hydroxy-2-(4-iodo-2-methyl-phenylamino)-N-isopropyl-benzamide;
N-Cyclopropylmethoxy-3,4,5-trifluoro-2-(4-iodo-2-methyl-phenylamino)-benzamide;
4-Fluoro-N-hydroxy-2-(4-iodo-2-methyl-phenylamino)-N-methyl-benzamide;
4-Fluoro-N-hydroxy-2-(4-iodo-2-methyl-phenylamino)-5-nitro-benzamide;
2-(2-Chloro-4-iodo-phenylamino)-N-hydroxy-4-nitro-benzamide;
3,4-Difluoro-N-hydroxy-2-(4-iodo-2-methyl-phenylamino)-benzamide;
2-(2-Chloro-4-iodo-phenylamino)-4-fluoro-N-hydroxy-benzamide (HCl salt);
2-(2-Chloro-4-iodo-phenylamino)-4-fluoro-N-(tetrahydropyran-2-yloxy)-benzamide;
3,4-Difluoro-2-(2-chloro-4-iodo-phenylamino)-N-cyclobutylmethoxy-benzamide;
5-Bromo-2-(2-chloro-4-iodo-phenylamino)-N-(2-dimethylamino-ethoxy)-3,4-difluoro-benzamide monohydrochloride salt;
5-Bromo-2-(2-chloro-4-iodo-phenylamino)-3,4-difluoro-N-hydroxy-benzamide;
3,4-Difluoro-2-(2-chloro-4-iodo-phenylamino)-N-cyclopropylmethoxy-benzamide;
5-Bromo-2-(2-chloro-4-iodo-phenylamino)-N-cyclopropylmethoxy-3,4-difluoro-benzamide;
5-Bromo-N-cyclohexylmethoxy-3,4-difluoro-2-(4-iodo-2-methyl-phenylamino)-benzamide;
5-Bromo-N-cyclopentylmethoxy-3,4-difluoro-2-(4-iodo-2-methyl-phenylamino)-benzamide; and
5-Bromo-N-cyclobutylmethoxy-3,4-difluoro-2-(4-iodo-2-methyl-phenylamino)-benzamide.

This invention also provides pharmaceutical formulations comprising a compound of Formula I together with a pharmaceutically acceptable excipient, diluent, or carrier. Preferred formulations include any of the foregoing preferred compounds together with an excipient, diluent, or carrier.

The compounds of Formula I are potent and selective inhibitors of kinase enzymes, particularly $MEK_1$ and $MEK_2$. They are, therefore, useful to treat subjects suffering from cancer and other proliferative diseases such as psoriasis, restenosis, autoimmune disease, and atherosclerosis. The compounds are especially well-suited to treat cancers such as breast cancer, colon cancer, prostate cancer, skin cancer, and pancreatic cancer. The compounds can also be used to treat stroke, diabetes, hepatomegaly, cardiomegaly, Alzheimer's disease, cystic fibrosis, and viral disease. The invention provides a method of inhibiting MEK enzymes and the foregoing diseases by administering to a subject an effective amount of a compound of Formula I.

DETAILED DESCRIPTION OF THE INVENTION

As used herein, the term "aryl" means a cyclic, bicyclic, or tricyclic aromatic ring moiety having from five to twelve carbon atoms. Examples of typical aryl groups include phenyl, naphthyl, and fluorenyl. The aryl may be substituted by one, two, or three groups selected from fluoro, chloro, bromo, iodo, alkyl, hydroxy, alkoxy, nitro, or amino. Typical substituted aryl groups include 3-fluorophenyl, 3,5-dimethoxyphenyl, 4-nitronaphthyl, 2-methyl-4-chloro-7-aminofluorenyl, and the like.

The term "aryloxy" means an aryl group bonded through an oxygen atom, for example phenoxy, 3-bromophenoxy, naphthyloxy, and 4-methyl-1-fluorenyloxy.

"Heteroaryl" means a cyclic, bicyclic, or tricyclic aromatic ring moiety having from four to eleven carbon atoms and one, two, or three heteroatoms selected from O, S, or N. Examples include furyl, thienyl, pyrrolyl, pyrazolyl, triazolyl, thiazolyl, xanthenyl, pyronyl, indolyl, pyrimidyl, naphthyridyl, pyridyl, and triazinyl. The heteroaryl groups can be unsubstituted or substituted by one, two, or three groups selected from fluoro, chloro, bromo, iodo, alkyl, hydroxy, alkoxy, nitro, or amino. Examples of substituted heteroaryl groups include chloropyranyl, methylthienyl, fluoropyridyl, amino-1,4-benzisoxazinyl, nitroisoquinolinyl, and hydroxyindolyl.

The heteroaryl groups can be bonded through oxygen to make heteroaryloxy groups, for example thienyloxy, isothiazolyloxy, benzofuranyloxy, pyridyloxy, and 4-methylisoquinolinyloxy.

The term "$C_1$–$C_8$ alkyl" means straight and branched chain aliphatic groups having from one to eight carbon atoms. Typical $C_1$–$C_8$ alkyl groups include methyl, ethyl, isopropyl, tert.-butyl, 2,3-dimethylhexyl, and 1,1-dimethylpentyl. The alkyl groups can be unsubstituted or substituted by cycloalkyl, cycloalkyl containing a heteroatom selected from O, S, or $NR_9$, aryl, aryloxy, heteroaryl, or heteroaryloxy, as those terms are defined above. Examples of aryl and aryloxy substituted alkyl groups include phenylmethyl, 2-phenylethyl, 3-chlorophenylmethyl, 1,1-dimethyl-3-(2-nitrophenoxy)butyl, and 3,4,5-trifluoronaphthylmethyl. Examples of alkyl groups substituted by a heteroaryl or heteroaryloxy group include thienylmethyl, 2-furylethyl, 6-furyloxyoctyl, 4-methylquinolyloxymethyl, and 6-isothiazolylhexyl. Cycloalkyl substituted alkyl groups include cyclopropylmethyl, 2-cyclopentylethyl, 2-piperidin-1-yl-ethyl, 3-(tetrahydropyran-2-yl)propyl, and cyclobutylmethyl.

"$C_2$–$C_8$ Alkenyl" means a straight or branched carbon chain having one or more double bonds. Examples include but-2-enyl, 2-methyl-prop-2-enyl, 1,1-dimethyl-hex-4-enyl, 3-ethyl-4-methyl-pent-2-enyl, and 3-isopropyl-pent-4-enyl. The alkenyl groups can be substituted with aryl, aryloxy, heteroaryl, or heteroyloxy, for example 3-phenylprop-2-enyl, 6-thienyl-hex-2-enyl, 2-furyloxy-but-2-enyl, and 4-naphthyloxy-hex-2-enyl.

"$C_2$–$C_8$ Alkynyl" means a straight or branched carbon chain having from two to eight carbon atoms and at least one triple bond. Typical alkynyl groups include prop-2-ynyl, 2-methyl-hex-5-ynyl, 3,4-dimethyl-hex-5-ynyl, and 2-ethyl-but-3-ynyl. The alkynyl groups can be substituted by aryl, aryloxy, heteroaryl, or heteroaryloxy, for example 4-(2-fluorophenyl)-but-3-ynyl, 3-methyl-5-thienylpent-4-ynyl, 3-phenoxy-hex-4-ynyl, and 2-furyloxy-3-methyl-hex-4-ynyl.

The alkenyl and alkynyl groups can have one or more double bonds or triple bonds, respectively, or a combination of double and triple bonds. For example, typical groups having both double and triple bonds include hex-2-en-4-ynyl, 3-methyl-5-phenylpent-2-en-4-ynyl, and 3-thienyloxy-hex-3-en-5-ynyl.

The term "$C_3$–$C_{10}$ cycloalkyl" means a non-aromatic ring or fused rings containing from three to ten carbon atoms. Examples include cyclopropyl, cyclobutyl, cyclopenyl, cyclooctyl, bicycloheptyl, adamantyl, and cyclohexyl. The ring can optionally contain a heteroatom selected from O, S, or $NR_9$. Such groups include tetrahydrofuryl, tetrahydropyrrolyl, octahydrobenzofuranyl, octahydroindolyl, and octahydrobenzothiofuranyl.

$R_3$, $R_4$, and $R_5$ can include groups defined by the term (O or NH)$_m$—(CH$_2$)$_n$—$R_9$. Examples of such groups are aminomethyl, 2-aminoethyl, 2-aminoethylamino, 3-aminopropoxy, N,N-diethylamino, 3-(N-methyl-N-isopropylamino)-propylamino, 2-(N-acetylamino)-ethoxy, 4-(N-dimethylaminocarbonylamino)-butoxy, and 3-(N-cyclopropylamino)-propoxy.

The 4-bromo and 4-iodo phenylamino benzhydroxamic acid derivatives of Formula I can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a phenylamino benzoic acid, and then reacting the benzoic acid phenylamino derivative with a hydroxylamine derivative. This process is depicted in Scheme 1.

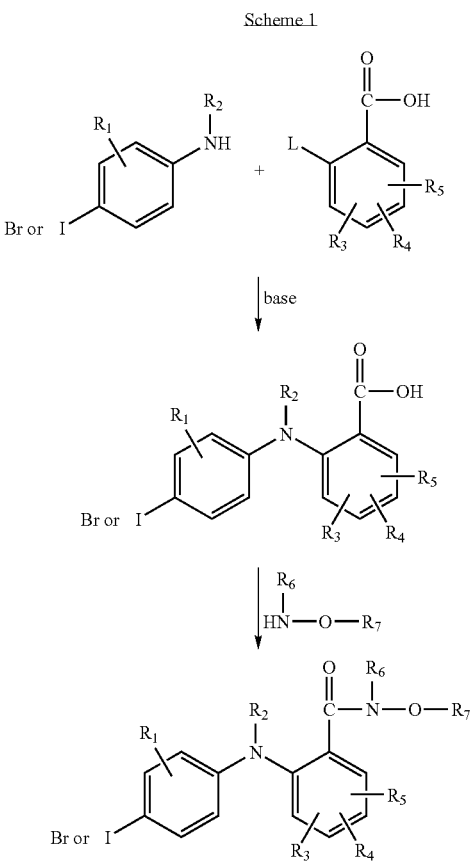

where L is a leaving group, for example halo such as fluoro, chloro, bromo or iodo, or an activated hydroxy group such as a diethylphosphate, trimethylsilyloxy, p-nitrophenoxy, or phenylsulfonoxy.

The reaction of the aniline derivative and the benzoic acid derivative generally is accomplished by mixing the benzoic acid with an equimolar quantity or excess of the aniline in an unreactive organic solvent such as tetrahydrofuran, or toluene, in the presence of a base such as lithium diisopropylamide, n-butyl lithium, sodium hydride, and sodium amide. The reaction generally is carried out at a temperature of about −78° C. to about 25° C., and normally is complete within about 2 hours to about 4 days. The product can be isolated by removing the solvent, for example by evaporation under reduced pressure, and further purified, if desired, by standard methods such as chromatography, crystallization, or distillation.

The phenylamino benzoic acid next is reacted with a hydroxylamine derivative HNR$_6$OR$_7$ in the presence of a peptide coupling reagent. Hydroxylamine derivatives that can be employed include methoxylamine, N-ethyl-isopropoxy amine, and tetrahydro-oxazine. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP) and (benzotriazolyloxy)tripyrrolidino phosphonium hexafluorophosphate (PyBOP). The phenylamino benzoic acid and hydroxylamino derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

An alternative method for making the invention compounds involves first converting a benzoic acid to a hydroxamic acid derivative, and then reacting the hydroxamic acid derivative with an aniline. This synthetic sequence is depicted in Scheme 2.

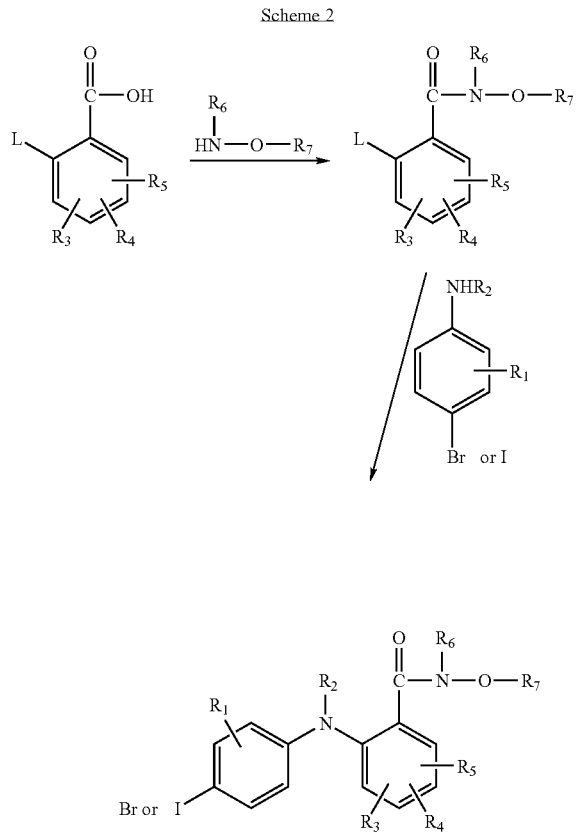

where L is a leaving group. The general reaction conditions for both of the steps in Scheme 2 are the same as those described above for Scheme 1.

Yet another method for making invention compounds comprises reacting a phenylamino benzhydroxamic acid with an ester forming group as depicted in Scheme 3.

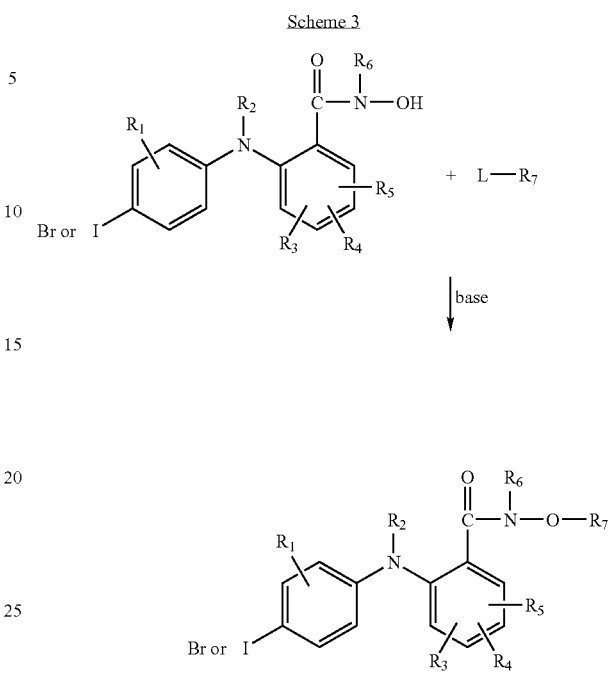

where L is a leaving group such as halo, and a base is triethylamine or diisopropylamine.

The synthesis of invention compounds of Formula I is further illustrated by the following detailed examples.

EXAMPLE 1

4-Fluoro-N-hydroxy-2-(4-iodo-2-methyl-phenylamino)-benzamide (a) Preparation of 4-Fluoro-2-(4-iodo-2-methyl-phenylamino)-benzoic acid To a stirred solution containing 3.16 g (0.0133 mol) of 2-amino-5-iodotoluene in 5 mL of tetrahydrofuran at −78° C. was added 10 mL (0.020 mol) of a 2.0 M lithium diisopropylamide in tetrahydrofuran/heptane/ethylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofuran was added. The reaction temperature was allowed to increase slowly to room temperature, at which temperature the mixture was stirred for 2 days. The reaction mixture was concentrated by evaporation of the solvent under reduced pressure. Aqueous HCl (10%) was added to the concentrate, and the solution was extracted with dichloromethane. The organic phase was dried (MgSO$_4$) and then concentrated over a steambath to low volume (10 mL) and cooled to room temperature. The off-white fibers which formed were collected by vacuum filtration, rinsed with hexane, and dried in a vacuum-oven (76° C.; ca. 10 mm of Hg) to afford 1.10 g (47%) of the desired material; mp 224–229.5° C.;

$^1$H NMR (400 MHz, DMSO): δ 9.72 (s, 1H), 7.97 (dd, 1H, J=7.0, 8.7 Hz), 7.70 (d, 1H, J=1.5 Hz), 7.57 (dd, 1H, J=8.4, 1.9 Hz), 7.17 (d, 1H, J=8.2 Hz), 6.61–6.53 (m, 2H), 2.18 (s, 3H); $^{13}$C NMR (100 MHz, DMSO): δ 169.87, 166.36 (d, J$_{C-F}$=249.4 Hz), 150.11 (d, J$_{C-F}$=11.4 Hz), 139.83, 138.49, 136.07, 135.26 (d, $J_{C-F}$=11.5 Hz), 135.07, 125.60, 109.32, 104.98 (d, $J_{C-F}$=21.1 Hz), 99.54 (d, $J_{C-F}$=26.0 Hz), 89.43, 17.52; $^{19}$F NMR (376 MHz, DMSO): δ −104.00 to −104.07 (m); IR (KBr) 1670 (C=O stretch) cm$^{-1}$; MS (CI) M+1=372. Analysis calculated for $C_{14}H_{11}FINO_2$: C, 45.31; H, 2.99; N, 3.77. Found: C, 45.21; H, 2.77; N, 3.64.

(b) Preparation of 4-Fluoro-N-hydroxy-2-(4-iodo-2-methyl-phenylamino)-benzamide

To a stirred solution of 4-fluoro-2-(4-iodo-2-methyl-phenylamino)-benzoic acid (0.6495 g, 0.001750 mol), O-(tetrahydro-2H-pyran-2-yl)-hydroxylamine (0.2590 g, 0.002211 mol), and diisopropylethylamine (0.40 mL, 0.0023 mol) in 31 mL of an equivolume tetrahydrofuran-dichloromethane solution was added 1.18 g (0.00227 mol) of solid PyBOP ([benzotriazolyloxy]tripyrrolidino phosphonium hexafluorophosphate, Advanced ChemTech) directly. The reaction mixture was stirred for 30 minutes after which time it was concentrated in vacuo. The brown oil was treated with 10% aqueous hydrochloric acid. The suspension was extracted with ether. The organic extraction was washed with 10% sodium hydroxide followed by another 10% hydrochloric acid wash, was dried (MgSO$_4$) and concentrated in vacuo to afford 1.0 g of a light-brown foam. This intermediate was dissolved in 25 mL of ethanolic hydrogen chloride, and the solution was allowed to stand at room temperature for 15 minutes. The reaction mixture was concentrated in vacuo to a brown oil that was purified by flash silica chromatography. Elution with dichloromethane→dichloromethane-methanol (166:1) afforded 0.2284 g of a light-brown viscous oil. Scratching with pentane-hexanes and drying under high vacuum afforded 0.1541 g (23%) of an off-white foam; mp 61–75° C.;

$^1$H NMR (400 MHz, DMSO): δ 11.34 (s, 1H), 9.68 (s, 1H), 9.18 (s, 1H), 7.65 (d, 7.58 (dd, 1H, J=8.7, 6.8 Hz), 7.52 (dd, 1H, J=8.4, 1.9 Hz), 7.15 (d, 1H, J=8.4 Hz), J=11.8, 2.4 Hz), 6.62 (ddd, 1H, J=8.4, 8.4, 2.7 Hz), 2.18 (s, 3H); $^{13}$C NMR (100 MHz, DMSO): δ 165.91, 164.36 (d, $J_{C-F}$=247.1 Hz), 146.78, 139.18, 138.77, 135.43, 132.64, 130.60 (d, $J_{C-F}$=11.5 Hz), 122.23, 112.52, 104.72 (d, J=22.1 Hz), 100.45 (d, $J_{C-F}$=25.2 Hz), 86.77, 17.03; $^{19}$F NMR (376 MHz, DMSO): δ −107.20 to −107.27 (m); IR (KBr) 3307 (broad, O—H stretch), 1636 (C=O stretch) cm$^{-1}$; MS (CI) M+1=387. Analysis calculated for $C_{14}H_{12}FIN_2O_2$: C, 43.54; H, 3.13; N, 7.25. Found: C, 43.62; H, 3.24; N, 6.98.

EXAMPLE 2

5-Bromo-3,4-difluoro-N-hydroxy-2-(4-iodo-2-methyl-phenylamino)-benzamide (a) Preparation of 5-Bromo-2,3,4-trifluorobenzoic acid To a stirred solution comprised of 1-bromo-2,3,4-trifluorobenzene (Aldrich, 99%; 5.30 g, 0.0249 mol) in 95 mL of anhydrous tetrahydrofuran cooled to −78° C. was slowly added 12.5 mL of 2.0 M lithium diisopropylamide in heptane/tetrahydrofuran/ethylbenzene solution (Aldrich). The mixture was stirred for 1 hour and transferred by canula into 700 mL of a stirred saturated ethereal carbon dioxide solution cooled to −78° C. The cold bath was removed, and the reaction mixture was stirred for 18 hours at ambient temperature. Dilute (10%) aqueous hydrochloric acid (ca. 500 mL) was poured into the reaction mixture, and the mixture was subsequently concentrated on a rotary evaporator to a crude solid. The solid product was partitioned between diethyl ether (150 mL) and aq. HCl (330 mL, pH 0). The aqueous phase was extracted with a second portion (100 mL) of diethyl ether, and the combined ethereal extracts were washed with 5% aqueous sodium hydroxide (200 mL) and water (100 mL, pH 12). These combined alkaline aqueous extractions were acidified to pH 0 with concentrated aqueous hydrochloric acid. The resulting suspension was extracted with ether (2×200 mL). The combined organic extracts were dried (MgSO$_4$), concentrated in vacuo, and subjected to high vacuum until constant mass was achieved to afford 5.60 g (88% yield) of an off-white powder; mp 139–142.5° C.;

$^1$H NMR (400 MHz, DMSO): δ 13.97 (broad s, 1H, 8.00–7.96 (m, 1H); $^{13}$C NMR (100 MHz, DMSO): δ 162.96, 129.34, 118.47, 104.54 (d, $J_{C-F}$=22.9 Hz); $^{19}$F NMR (376 MHz, DMSO): δ −120.20 to −120.31 (m), −131.75 to −131.86 (m), −154.95 to −155.07 (m); IR (KBr) 1696 (C=O stretch)cm$^{-1}$; MS (CI) M+1=255. Analysis calculated for $C_{74}H_{21}BrF_3O_2$: C, 32.97; H, 0.79; N, 0.00; Br, 31.34; F, 22.35. Found: C, 33.18; H, 0.64; N, 0.01; Br, 30.14; F, 22.75.

(b) Preparation of 5-Bromo-3,4-difluoro-2-(4-iodo-2-methyl-phenylamino)-benzoic acid To a stirred solution comprised of 1.88 g (0.00791 mol) of 2-amino-5-iodotoluene in 10 mL of tetrahydrofuran at −78° C. was added 6 mL (0.012 mol) of a 2.0 M lithium diisopropylamide in tetrahydrofuran/heptane/ethylbenzene (Aldrich) solution. The resulting green suspension was stirred vigorously for 10 minutes, after which time a solution of 1.00 g (0.00392 mol) of 5-bromo-2,3,4-trifluorobenzoic acid in 15 mL of tetrahydrofuran was added. The cold bath was subsequently removed, and the reaction mixture stirred for 18 hours. The mixture was concentrated, and the concentrate was treated with 100 mL of dilute (10%) aqueous hydrochloric acid. The resulting suspension was extracted with ether (2×150 mL), and the combined organic extractions were dried (MgSO$_4$) and concentrated in vacuo to give an orange solid. The solid was triturated with boiling dichloromethane, cooled to ambient temperature, and collected by filtration. The solid was rinsed with dichloromethane, and dried in the vacuum-oven (80° C.) to afford 1.39 g (76%) of a yellow-green powder; mp 259.5–262° C.;

$^1$H NMR (400 MHz, DMSO): δ 9.03 (s, 1H), 7.99 (dd, 1H, J=7.5, 1.9 Hz), 7.57 (dd, 1H, J=1.5 Hz), 7.42 (dd, 1H, J=8.4, 1.9 Hz), 6.70 (dd, 1H, J=8.4, 6.0 Hz), 2.24 (s, 3H); $^{19}$F NMR (376 MHz, DMSO): δ −123.40 to −123.47 (m); −139.00 to −139.14 (m); IR (KBr) 1667 (C=O stretch) cm$^{-1}$; MS (CI) M+1=469. Analysis calculated for $C_{14}H_9BrF_{21}NO_2$: C, 35.93; H, 1.94; N, 2.99; Br, 17.07; F, 8.12; I, 27.11. Found: C, 36.15; H, 1.91; N, 2.70; Br, 16.40; F, 8.46; I, 26.05.

(c) Preparation of 5-Bromo-3,4-difluoro-N-hydroxy-2-(4-iodo-2-methyl-phenylamino)-benzamide To a stirred solution comprised of 5-bromo-3,4-difluoro-2-(4-iodo-2-methyl-phenylamino)-benzoic acid (0.51 g, 0.0011 mol), O-(tetrahydro-2H-pyran-2-yl)-hydroxylamine (0.15 g, 0.0013 mol), and diisopropylethylamine (0.25 mL, 0.0014 mol) in 20 mL of an equivolume tetrahydrofuran-dichloromethane solution was added 0.6794 g (0.001306 mol) of solid PyBOP (Advanced ChemTech) directly. The reaction mixture was stirred at 24° C. for 10 minutes, and then was concentrated to dryness in vacuo. The concentrate was suspended in 100 mL of 10% aqueous hydrochloric acid. The suspension was extracted with 125 mL of diethyl ether. The ether layer was separated, washed with 75 mL of 10% aqueous sodium hydroxide, and then with 100 mL of dilute acid. The ether solution was dried (MgSO$_4$) and concentrated in vacuo to afford 0.62 g (100%) of an off-white foam. The foam was dissolved in ca. 15 mL of methanolic hydrogen chloride. After 5 minutes, the solution was concentrated in vacuo to an oil, and the oil was purified by flash silica chromatography. Elution with dichloromethane→dichloromethane-methanol (99:1) afforded 0.2233 g (42%) of a yellow powder. The powder was dissolved in diethyl ether and washed with dilute hydrochloric acid. The organic phase was dried (MgSO$_4$) and concentrated in vacuo to afford 0.200 g of a foam. This product was triturated with pentane to afford 0.1525 g of a powder that was repurified by flash silica chromatography. Elution with dichloromethane afforded 0.0783 g (15%) of an analytically pure title compound, mp 80–90° C.;

$^1$H NMR (400 MHz, DMSO): δ 11.53 (s, 1H), 9.38 (s, 1H), 8.82 (s, 1H), 7.70 (dd, 1H, J=7.0, 1.9 Hz), 7.53 (s, 1H), 7.37 (dd, 1H, J=8.4, 1.9 Hz), 6.55 (dd, 1H, J=8.2, 6.5 Hz), 2.22(s, 3H); $^{19}$F NMR (376 MHz, DMSO): 8-126.24 to −126.29 (m), −137.71 to −137.77 (m); IR (KBr) 3346 (broad, O—H stretch), 1651 (C=O stretch)cm$^{-1}$; MS (CI) M+1=484. Analysis calculated for $C_{14}H_{10}BrF_{21}N_2O_2$: C, 34.81; H, 2.09; N, 5.80. Found: C, 34.53; H, 1.73; N, 5.52, Examples 3 to 12 and 78 to 102 in the table below were prepared by the general procedures of Examples 1 and 2.

EXAMPLES 13–77

Examples 13 to 77 were prepared utilizing combinatorial synthetic methodology by reacting appropriately substituted phenylamino benzoic acids (e.g., as shown in Scheme 1) and hydroxylamines

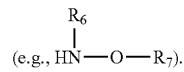

A general method is given below:

To a 0.8 mL autosampler vial in a metal block was added 40 μL of a 0.5 M solution of the acid in DMF and 40 μL of the hydroxylamine (2 M solution in Hunig's base and 1 M in amine in DMF). A 0.5 M solution of PyBrop was freshly prepared, and 50 μL were added to the autosampler vial. The reaction was allowed to stand for 24 hours.

The reaction mixture was transferred to a 2 dram vial and diluted with 2 mL of ethyl acetate. The organic layer was washed with 3 mL of distilled water and the water layer washed again with 2 mL of ethyl acetate. The combined organic layers were allowed to evaporate to dryness in an open fume hood.

The residue was taken up in 2 mL of 50% acetonitrile in water and injected on a semi-prep reversed phase column (10 mm×25 cm, 5 μM spherical silica, pore Size 115 A derivatised with C-18, the sample was eluted at 4.7 mL/min with a linear ramp to 100% acetonitrile over 8.5 minutes. Elution with 100% acetonitrile continued for 8 minutes.) Fractions were collected by monitoring at 214 nM. The desired fractions were evaporated using a Zymark Turbovap. The product was dissolved in chloroform and transferred to a preweighed vial, evaporated, and weighed again to determine the yield. The structure was confirmed by mass spectroscopy.

EXAMPLES 3–102

| Example No. | Compound | Melting Point (° C.) | MS (M − H$^+$) |
|---|---|---|---|
| 3 | 2-(4-bromo-2-methyl-phenylamino)-4-fluoro-N-hydroxy-benzamide | 56–75 dec | 523 |
| 4 | 5-Chloro-N-hydroxy-2-(4-iodo-2-methyl-phenylamino)-benzamide | 65 dec | |
| 5 | 5-Chloro-N-hydroxy-2-(4-iodo-2-methyl-phenylamino)-N-methyl-benzamide | 62–67 | |
| 6 | 5-Chloro-2-(4-iodo-2-methyl-phenylamino)-N-(terahydropyran-2-yloxy)benzamide | 105–108 | |
| 7 | 5-Chloro-2-(4-iodo-2-methyl-phenylamino)-N-methoxybenzamide | 64–68 | |
| 8 | 4-Fluoro-N-hydroxy-2-(4-fluoro-2-methyl-phenylamino)-benzamide | 119–135 | |
| 9 | 4-Fluoro-N-hydroxy-2-(2-methyl phenylamino)-benzamide | 101–103 | |
| 10 | 4-Fluoro-2-(4-fluor-2-methyl-phenylamino)-N-(terahydropyran-2-yloxy)benzamide | 142–146 | |
| 11 | 4-Fluoro-N-hydroxy-2-(4-cluoro-2-methyl-phenylamino)-benzamide | 133.5–135 | |
| 12 | 4-Fluoro-2-(4-iodo-2-methyl-phenylamino)-N-phenylmethoxy-benzamide | 107–109.5 | |
| 13 | 4-Fluoro-2-(4-iodo-2-methyl-phenylamino)-N-methoxy-benzamide | | 399 |
| 14 | 3,4-Difluoro-2-(4-iodo-2-methyl-phenylamino)-N-methoxy-benzamide | | 417 |
| 15 | 2-(4-Bromo-2-methyl-phenylamino)-3,4-difluoro-N-methoxy-benzamide | | 369 |
| 16 | 2-(4-Bromo-2-methyl-phenylamino)-N-ethoxy-3,4-difluoro-benzamide | | 342* (M-EtO) |
| 17 | 5-Bromo-N-ethoxy-3,4-difluoro-2-(4-iodo-2-methyl-phenylamino)-benzamide | | 509 |

-continued

EXAMPLES 3–102

| Example No. | Compound | Melting Point (° C.) | MS (M − H$^+$) |
|---|---|---|---|
| 18 | 3,4-Difluoro-2-(4-iodo-2-methyl-phenylamino)-N-isopropoxy-benzamide | | 445 |
| 19 | 2-(4-Bromo-2-methyl-phenylamino)-3,4-difluoro-N-isopropoxy-benzamide | | 397 |
| 20 | 4-Fluoro-N-(furan-3-ylmethoxy)-2-(4-iodo-2-methyl-phenylamino)-benzamide | | 465 |
| 21 | 3,4-Difluoro-N-(furan-3-ylmethoxy)-2-(4-iodo-2-methyl-phenylamino)-benzamide | | 483 |
| 22 | 2-(4-Bromo-2-methyl-phenylamino)-3,4-difluoro-N-(furan-3-ylmethoxy)-benzamide | | 435 |
| 23 | 5-Bromo-3,4-difluoro-N-(furan-3-ylmethoxy)-2-(4-iodo-2-methyl-phenylamino)-benzamide | | 561 |
| 24 | 5-Bromo-N-(but-2-enyloxy)-3,4-difluoro-2-(4-iodo-2-methyl-phenylamino)-benzamide | | 536 |
| 25 | 4-Fluoro-2-(4-iodo-2-methyl-phenylamino)-N-(prop-2-ynyloxy)-benzamide | | 423 |
| 26 | 3,4-Difluoro-2-(4-iodo-2-methyl-phenylamino)-N-(prop-2-ynyloxy)-benzamide | | 441 |
| 27 | 3,4-Difluoro-2-(4-iodo-2-methyl-phenylamino)-N-(1-methyl-prop-2-ynyloxy)-benzamide | | 455 |
| 28 | 2-(4-Bromo-2-methyl-phenylamino)-3,4-difluoro-N-(1-methyl-prop-2-ynyloxy)-benzamide | | 407 |
| 29 | N-(But-3-ynyloxy)-3,4-difluoro-2-(4-iodo-2-methyl-phenylamino)-benzamide | | 455 |
| 30 | 2-(4-Bromo-2-methyl-phenylamino)-N-(but-3-ynyloxy)-3,4-difluoro-benzamide | | 407 |
| 31 | 5-Bromo-N-(but-3-ynyloxy)-3,4-difluoro-2-(4-iodo-2-methyl-phenylamino)-benzamide | | 533 |
| 32 | 3,4-Difluoro-2-(4-iodo-2-methyl-phenylamino)-N-(3-phenyl-prop-2-ynyloxy)-benzamide | | 517 |
| 33 | 3,4-Difluoro-2-(4-bromo-2-methyl-phenylamino)-N-(3-phenyl-prop-2-ynyloxy)-benzamide | | 469 |
| 34 | 3,4-Difluoro-N-[3-(3-fluoro-phenyl)-prop-2-ynyloxy]-2-(4-iodo-2-methyl-phenylamino)-benzamide | | 535 |
| 35 | 2-(4-Bromo-2-methyl-phenylamino)-3,4-difluoro-N-[3-(3-fluoro-phenyl)-prop-2-ynyloxy]-benzamide | | 487 |
| 36 | 3,4-Difluoro-N-[3-(2-fluoro-phenyl)-prop-2-ynyloxy]-2-(4-iodo-2-methyl-phenylamino)-benzamide | | 535 |
| 37 | 5-Bromo-3,4-difluoro-N-[3-(2-fluoro-phenyl)-prop-2-ynyloxy]-2-(4-iodo-2-methyl-phenylamino)-benzamide | | 613 |
| 39 | 2-(4-Bromo-2-methyl-phenylamino)-3,4-difluoro-N-(3-methyl-5-phenyl-pent-2-en-4-ynyloxy)-benzamide | | 510 |
| 40 | N-Ethoxy-3,4-difluoro-2-(4-iodo-2-methyl-phenylamino)-benzamide | | 431 |
| 41 | 2-(4-Bromo-2-methyl-phenylamino)-N-ethoxy-3,4-difluoro-benzamide | | 383 |
| 42 | 4-Fluoro-2-(4-iodo-2-methyl-phenylamino)-N-propoxy-benzamide | | 427 |
| 43 | 3,4-Difluoro-2-(4-iodo-2-methyl-phenylamino)-N-propoxy-benzamide | | 445 |
| 44 | 2-(4-Bromo-2-methyl-phenylamino)-3,4-difluoro-N-propoxy-benzamide | | 397 |
| 45 | 5-Bromo-3,4-difluoro-2-(4-iodo-2-methyl-phenylamino)-N-propoxy-benzamide | | 523 |
| 46 | 4-Fluoro-2-(4-iodo-2-methyl-phenylamino)-N-isopropoxy-benzamide | | 427 |
| 47 | 3,4-Difluoro-2-(4-iodo-2-methyl-phenylamino)-N-isopropoxy-benzamide | | 445 |
| 48 | 2-(4-Bromo-2-methyl-phenylamino)-3,4-difluoro-N-isopropoxy-benzamide | | 397 |
| 49 | 5-Bromo-3,4-difluoro-2-(4-iodo-2-methyl-phenylamino)-N-isopropoxy-benzamide | | 523 |
| 50 | N-Cyclobutyloxy-3,4-difluoro-2-(4-iodo-2-methyl-phenylamino)-benzamide | | 457 |
| 51 | 2-(4-Bromo-2-methyl-phenylamino)-N-cyclobutyloxy-3,4-difluoro-benzamide | | 409 |

-continued

EXAMPLES 3–102

| Example No. | Compound | Melting Point (° C.) | MS (M − H$^+$) |
|---|---|---|---|
| 52 | N-Cyclopentyloxy-4-fluoro-2-(4-iodo-2-methyl-phenylamino)-benzamide | | 453 |
| 53 | N-Cyclopentyloxy-3,4-difluoro-2-(4-iodo-2-methyl-phenylamino)-benzamide | | 471 |
| 54 | 2-(4-Bromo-2-methyl-phenylamino)-N-cyclopentyloxy-3,4-difluoro-benzamide | | 423 |
| 55 | N-Cyclopropylmethoxy-4-fluoro-2-(4-iodo-2-methyl-phenylamino)-benzamide | | 439 |
| 56 | N-Cyclopropylmethoxy-3,4-difluoro-2-(4-iodo-2-methyl-phenylamino)-benzamide | | 457 |
| 57 | 2-(4-Bromo-2-methyl-phenylamino)-N-cyclopropylmethoxy-3,4-difluoro-benzamide | | 409 |
| 58 | 5-Bromo-N-cyclopropylmethoxy-3,4-difluoro-2-(4-iodo-2-methyl-phenylamino) | | 435 |
| 59 | 4-Fluoro-2-(4-iodo-2-methyl-phenylamino)-N-(2-phenoxy-ethoxy)-benzamide | | 505 |
| 60 | 3,4-Difluoro-2-(4-iodo-2-methyl-phenylamino)-N-(2-phenoxy-ethoxy)-benzamide | | 523 |
| 61 | 2-(4-Bromo-2-methyl-phenylamino)-3,4-difluoro-N-(2-phenoxy-ethoxy)-benzamide | | 475 |
| 62 | 4-Fluoro-2-(4-iodo-2-methyl-phenylamino)-N-(thiophen-2-ylmethoxy)-benzamide | | 481 |
| 63 | 3,4-Difluoro-2-(4-iodo-2-methyl-phenylamino)-N-(thiophen-2-ylmethoxy)-benzamide | | 499 |
| 64 | 2-(4-Bromo-2-methyl-phenylamino)-3,4-difluoro-N-(thiophen-2-ylmethoxy)-benzamide | | 451 |
| 65 | 4-Fluoro-2-(4-iodo-2-methyl-phenylamino)-N-(2-methyl-allyloxy)-benzamide | | 439 |
| 66 | 3,4-Difluoro-2-(4-iodo-2-methyl-phenylamino)-N-(2-methyl-allyloxy)-benzamide | | 457 |
| 67 | 2-(4-Bromo-2-methyl-phenylamino)-3,4-difluoro-N-(2-methyl-allyloxy)-benzamide | | 410 |
| 68 | N-(But-2-enyloxy)-4-fluoro-2-(4-iodo-2-methyl-phenylamino)-benzamide | | 439 |
| 69 | N-(But-2-enyloxy)-3,4-difluoro-2-(4-iodo-2-methyl-phenylamino)-benzamide | | 457 |
| 70 | 2-(4-Bromo-2-methyl-phenylamino)-N-(but-2-enyloxy)-3,4-difluoro-benzamide | | 410 |
| 71 | 3,4-Difluoro-2-(4-iodo-2-methyl-phenylamino)-N-(prop-2-ynyloxy)-benzamide | | 441 |
| 72 | N-(But-3-ynyloxy)-3,4-difluoro-2-(4-iodo-2-methyl-phenylamino)-benzamide | | 455 |
| 73 | 2-(4-Bromo-2-methyl-phenylamino)-N-(4,4-dimethyl-pent-2-ynyloxy)-3,4-difluoro-benzamide | | 449 |
| 74 | N-(But-2-enyloxy)-3,4-difluoro-2-(4-iodo-2-methyl-phenylamino)-benzamide | | 457 |
| 75 | 2-(4-Bromo-2-methyl-phenylamino)-N-(but-2-enyloxy)-3,4-difluoro-benzamide | | 410 |
| 76 | N-(3-tert.-butyl-propyn-2-yl)oxy-4-fluoro-2-(4-iodo-2-methyl-phenylamino)-benzamide | | 479 |
| 77 | 4-Fluoro-2-(4-iodo-2-methyl-phenylamino)-N-phenylmethoxy-benzamide | | 577* *CI |
| 78 | 4-Fluoro-N-hydroxy-2-(4-iodo-2-methyl-phenylamino)-N-isopropyl-benzamide | oil | |
| 79 | N-Cyclopropylmethoxy-3,4,5-trifluoro-2-(4-iodo-2-methyl-phenylamino)-benzamide | 125–127 | |
| 80 | 4-Fluoro-N-hydroxy-2-(4-iodo-2-methyl-phenylamino)-N-methyl-benzamide | 45–55 | |
| 81 | 4-Fluoro-N-hydroxy-2-(4-iodo-2-methyl-phenylamino)-5-nitro-benzamide | 208–209 (GLASS) | |
| 82 | 2-(2-Chloro-4-iodo-phenylamino)-N-hydroxy-4-nitro-benzamide | 199–200 | |
| 83 | 3,4-Difluoro-2-(4-iodo-2-methyl-phenylamino)-N-(tetrahydro-pyran-2-yloxy)-benzamide | 163–165 | |
| 84 | 3,4-Difluoro-N-hydroxy-2-(4-iodo-2-methyl-phenylamino)-benzamide | 65–75 | |
| 85 | 3,4-Difluoro-5-bromo-2-(4-iodo-2-methyl-phenylamino)-N-(2-piperidin-1-yl-ethoxy)-benzamide | 95 | |
| 86 | 5-Bromo-3,4-difluoro-2-(4-iodo-2-methyl-phenylamino)-N-(tetrahydro-pyran-2-yloxy)-benzamide | 167–169 | |

-continued

EXAMPLES 3–102

| Example No. | Compound | Melting Point (° C.) | MS (M − H+) |
|---|---|---|---|
| 87 | 2-(2-Chloro-4-iodo-phenylamino)-4-fluoro-N-hydroxy-benzamide (HCl salt) | 165–169 | |
| 88 | 2-(2-Chloro-4-iodo-phenylamino)-4-fluoro-N-(tetrahydro-pyran-2-yloxy)-benzamide | 166–167.5 | |
| 89 | 3,4-Difluoro-2-(2-chloro-4-iodo-phenylamino)-N-cyclobutylmethoxy-benzamide | 173–174 | |
| 90 | 3,4-Difluoro-2-(2-chloro-4-iodo-phenylamino)-N-(tetrahydro-pyran-2-yloxy)-benzamide | 121–122 | |
| 91 | 5-Bromo-2-(2-chloro-4-iodo-phenylamino)-N-(2-dimethylamino-ethoxy)-3,4-difluoro-benzamide monohydrochloride salt | 206–211.5 DEC | |
| 92 | 5-Bromo-N-(2-dimethylamino-propoxy)-3,4-difluoro-2-(4-iodo-2-methyl-phenylamino)-benzamide | 95–105 | |
| 93 | 5-Bromo-2-(2-chloro-4-iodo-phenylamino)-3,4-difluoro-N-hydroxy-benzamide | 266–280 DEC | |
| 94 | 5-Bromo-2-(2-chloro-4-iodo-phenylamino)-3,4-difluoro-N-(tetrahydro-pyran-2-yloxy)-benzamide | 167.5–169.5 | |
| 95 | 3,4-Difluoro-2-(2-chloro-4-iodo-phenylamino)-N-cyclopropylmethoxy-benzamide | 172.5–173.5 | |
| 96 | 5-Bromo-2-(2-chloro-4-iodo-phenylamino)-N-cyclopropylmethoxy-3,4-difluoro-benzamide | 171–172.5 | |
| 97 | 5-Bromo-3,4-difluoro-2-(4-iodo-2-methyl-phenylamino)-N-(2-morpholin-4-yl-ethoxy)-benzamide | 173.5–175 | |
| 98 | 5-Bromo-N-(2-diethylamino-ethoxy)-3,4-difluoro-(4-iodo-2-methyl-phenylamino)-benzamide | 81 DEC | |
| 99 | 5-Bromo-3,4-difluoro-2-(4-iodo-2-methyl-phenylamino)-N-isobutoxy-benzamide | 126–128 | |
| 100 | 5-Bromo-N-cyclohexylmethoxy-3,4-difluoro-2-(4-iodo-2-methyl-phenylamino)-benzamide | 139–142 | |
| 101 | 5-Bromo-N-cyclopentylmethoxy-3,4-difluoro-2-(4-iodo-2-methyl-phenylamino)-benzamide | 113–115 | |
| 102 | 5-Bromo-N-cyclobutylmethoxy-3,4-difluoro-2-(4-iodo-2-methyl-phenylamino)-benzamide | 138–139 | |

The invention compounds are useful in treating cancer and other proliferative diseases by virtue of their selective inhibition of the dual specificity protein kinases MEK$_1$ and MEK$_2$. The invention compound has been evaluated in a number of biological assays which are normally utilized to establish inhibition of proteins and kinases, and to measure mitogenic and metabolic responses to such inhibition.

Enzyme Assays

Cascade Assay for Inhibitors of the MAP Kinase Pathway

Incorporation of $^{32}$P into myelin basic protein (MBP) was assayed in the presence of a glutathione S-transferase fusion protein containing p44MAP kinase (GST-MAPK) and a glutathione S-transferase fusion protein containing p45MEK (GST-MEK). The assay solution contained 20 mM HEPES, pH 7.4, 10 mM MgCl$_2$, 1 mM MnCl$_2$, 1 mM EGTA, 50 µM [γ-$^{32}$P]ATP, 10 µg GST-MEK, 0.5 µg GST-MAPK and 40 µg MBP in a final volume of 100 µL. Reactions were stopped after 20 minutes by addition of trichloroacetic acid and filtered through a GF/C filter mat. $^{32}$P retained on the filter mat was determined using a 1205 Betaplate. Compounds were assessed at 10 µM for ability to inhibit incorporation of $^{32}$P.

To ascertain whether compounds were inhibiting GST-MEK or GST MAPK, two additional protocols were employed. In the first protocol, compounds were added to tubes containing GST-MEK, followed by addition of GST-MAPK, MBP and [γ-$^{32}$P]ATP. In the second protocol, compounds were added to tubes containing both GST-MEK and GST-MAPK, followed by MBP and [γ-$^{32}$P]ATP. Compounds that showed activity in both protocols were scored as MAPK inhibitors, while compounds showing activity in only the first protocol were scored as MEK inhibitors.

In Vitro MAP Kinase Assay

Inhibitory activity was also confirmed in direct assays. For MAP kinase, 1 µg GST-MAPK was incubated with 40 µg MBP for 15 minutes at 30° C. in a final volume of 50 µL containing 50 mM Tris (pH 7.5), 10 µM MgCl$_2$, 2 µM EGTA, and 10 µM [γ-$^{32}$P]ATP. The reaction was stopped by addition of Laemmli SDS sample buffer and phosphorylated MBP resolved by electrophoresis on a 10% polyacrylamide gel. Radioactivity incorporated into MBP was determined by autoradiography, and subsequently by excision of the bands followed by scintillation counting.

In Vitro MEK Assay

For evaluation of direct MEK activity, 10 µg GST-MEK1 was incubated with 5 µg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations were 15 minutes at 30° C. in a final volume of 50 µL containing 50 mM Tris (pH 7.5), 10 µM MgCl$_2$, 2 µM EGTA, and 10 µM [γ-$^{32}$P]ATP. The reaction was stopped by addition of Laemmli SDS sample buffer and phosphorylated GST-MAPK-KA was resolved by electrophoresis on a 10% polyacrylamide gel. Radioactivity incorporated into GST-MAPK-KA was determined by autoradiography, and subsequently by excision of the bands followed by scintillation counting. Additionally, an artificially activated MEK was utilized that contained serine to glutamate mutations at positions 218 and 222 (GST-MEK-2E). When these sites are phosphorylated, MEK activity is increased. Phosphorylation of these sites can be mimicked by mutation of the serine residues to glutamate. For this assay, 5 μg GST-MEK-2E was incubated with 5 μg GST-MAPK-KA for 15 minutes at 30° C. in the same reaction buffer as described above. Reactions were terminated and analyzed as above.

Whole Cell MAP Kinase Assay

To determine if compounds were able to block activation of MAP kinase in whole cells, the following protocol was used: Cells were plated in multi-well plates and grown to confluence. Cells were then serum-deprived overnight. Cells were exposed to the desired concentrations of compound or vehicle (DMSO) for 30 minutes, followed by addition of a growth factor, eg, PDGF (100 ng/mL). After a 5-minute treatment with the growth factor, cells were washed with PBS, then lysed in a buffer consisting of 70 mM NaCl, 10 mM HEPES (pH 7.4), 50 mM glycerol phosphate, and 1% Triton X-100. Lysates were clarified by centrifugation at 13,000×g for 10 minutes. Five micrograms of the resulting supernatants were incubated with 10 μg microtubule associated protein-2 (Map2) for 15 minutes at 30° C. in a final volume of 25 μL containing 50 mM Tris (pH 7.4), 10 mM $MgCl_2$, 2 mM EGTA and 30 μM [γ-$^{32}$P]ATP. Reactions were terminated by addition of Laemmli sample buffer. Phosphorylated Map2 was resolved on 7.5% acrylamide gels and incorporated radioactivity determined by autoradiography and subsequent excision of the bands followed by scintillation counting.

Immunoprecipitation and Antiphosphotyrosine Immunoblots

To determine the state of tyrosine phosphorylation of cellular MAP kinase, cells were lysed, endogenous MAP kinase was immunoprecipitated with a specific antibody, and the resulting immunoprecipitate analyzed for the presence of phosphotyrosine as follows: confluent cells were serum-deprived overnight and treated with compounds and growth factors as described above. Cells were then scraped and pelleted at 13,000×g for 2 minutes. The resulting cell pellet was resuspended and dissolved in 100 μL of 1% SDS containing 1 mM $NaVO_4$. Following alternate boiling and vortexing to denature cellular protein, 900 μL RIPA buffer (50 mM Tris (pH 7.4), 150 mM NaCl, 1% Triton X-100, 0.1% deoxycholate, and 10 mM EDTA) was added. To this mixture was added 60 μL agarose beads coupled with rabbit immunoglobulin G and 60 μL Pansorbin cells in order to clear the lysate of nonspecific binding proteins. This mixture was incubated at 4° C. for 15 minutes then centrifuged at 13,000×g for 10 minutes. The resulting supernatant was transferred to fresh tubes and incubated with 10 μL of a polyclonal antisera raised against a fragment of MAP kinase for a minimum of 1 hour at 4° C. Seventy microliters of a slurry of agarose beads coupled with protein G and protein A was added and the incubation continued for an additional 30 minutes at 4° C. The beads were pelleted by centrifugation at 13,000×g for 5 minutes and washed three times with 1 mL RIPA buffer. Laemmli sample buffer was added to the final bead pellet. This mixture was boiled for 5 minutes then resolved on a 10% acrylamide gel. Proteins on the gel were transferred to a nitrocellulose membrane and nonspecific binding sites on the membrane blocked by incubation with 1% ovalbumin and 1% bovine serum albumin in TBST (150 mM NaCl, 10 mM Tris (pH 7.4), and 0.05% Tween 20). The membrane was then incubated with a commercially available antibody directed against phosphotyrosine. Antibody bound on the membrane was detected by incubation with $^{125}$I-protein A, followed by autoradiography.

Cell Growth Assays $^3$H-Thymidine Incorporation

Cells were plated in multi-well plates and grown to near confluence. The media was then removed and replaced with growth media containing 1% bovine serum albumin. After 24-hour serum starvation, compounds and specific growth factors were added and incubations continued for an additional 24 hours. During the final 2 hours, $^3$H-thymidine was added to the medium. To terminate the incubations, the medium was removed and cell layers washed twice with ice-cold phosphate-buffered saline. After the final wash, ice-cold 5% trichloroacetic acid was added and the cells incubated for 15 minutes at room temperature. The trichloroacetic acid solution was then removed and the cell layer washed three times with distilled water. After the final wash, the cell layer was solubilized by addition of 2% sodium dodecylsulfate. Radioactivity in this solution was determined by scintillation counting.

In 3T3-L1 adipocyte cells, in which the inhibition blocks MAPK activation by insulin with an $IC_{50}$ of 3 μM, the compound had no effect on the insulin stimulated uptake of radiolabeled 2-deoxyglucose, or on the insulin-stimulated synthesis of either lipid or glycogen at 10 μM concentration. This demonstrates that the inhibitor shows selectivity between the mitogenic and metabolic effects of insulin, and demonstrates that the inhibitor will show less toxicity than an inhibitor which does not show this surprising selectivity.

Monolayer Growth

Cells were plated into multi-well plates at 10 to 20,000 cells/mL. Forty-eight hours after seeding, compounds were added to the cell growth medium and incubation was continued for 2 additional days. Cells were then removed from the wells by incubation with trypsin and enumerated with a Coulter counter.

Growth in Soft-Agar

Cells were seeded into 35-mm dishes at 5 to 10,000 cells/dish using growth medium containing 0.3% agar. After chilling to solidify the agar, cells were transferred to a 37° C. incubator. After 7 to 10 days growth, visible colonies were manually enumerated with the aid of a dissecting microscope.

Order of addition experiments established that the invention compounds are inhibiting MEK and not MAP kinase. Experiments looking at the phosphorylation of a kinase defective mutant of MAP kinase as substrate (so that there can be no autophosphorylation of the MAP kinase to complicate interpretation) confirms that the inhibitor inhibits MEK with an $IC_{50}$ essentially identical to that produced in the cascade assay.

Kinetic analysis demonstrates that the invention compounds are not competitive with ATP. Thus, they do not bind at the ATP binding site of the enzyme, which is probably the explanation as to why these compounds do not show the nonspecific kinase inhibitory activity typical of most kinase inhibitors, which do bind at the ATP binding site and which are ATP competitive.

The in vitro and in vivo biological activity of several representative compounds of Formula I in the foregoing assays is presented in Table 1. Data for several known compounds is also presented.

TABLE 1

| Compound of Example No. | In vitro IC$_{50}$ (μM) | In vivo (cell culture) IC$_{50}$ (μM) |
|---|---|---|
| 1 | 0.007 | 0.05 |
| 2 | 0.003 | 0.03 |
| 3 | 0.072 | 3 |
| 4 | 0.023 | 1 |
| 5 | 0.566 | ~30 |
| 6 | 0.345 | ~30 |
| 7 | 0.221 | <30 |
| 8 | 7.13 | 3 |
| 9 | 0.409 | 1 |
| 11 | 0.334 | 0.5 |
| 12 | 0.826 | |
| 13 | 0.243 | |
| 14 | 0.061 | >2 |
| 17 | 0.014 | |
| 20 | 0.042 | 0.17 |
| 21 | 0.014 | |
| 22 | 0.137 | |
| 23 | 0.016 | |
| 24 | 0.021 | 0.12 |
| 25 | 0.102 | |
| 27 | 0.026 | |
| 28 | 0.728 | |
| 29 | 0.076 | 0.73 |
| 30 | 0.971 | |
| 31 | 0.045 | |
| 32 | 0.017 | |
| 33 | 0.374 | |
| 34 | 0.113 | 1.5 |
| 36 | 0.056 | 0.07 |
| 37 | 0.002 | |
| 38 | 0.077 | 0.065 |
| 39 | 0.147 | |
| 40 | 0.028 | 0.125 |
| 41 | 0.236 | |
| 42 | 0.087 | |
| 43 | 0.040 | 0.100 |
| 44 | 0.475 | |
| 45 | 0.126 | |
| 47 | 0.087 | 0.13 |
| 49 | 0.085 | |
| 50 | 0.043 | 0.22 |
| 53 | 0.140 | |
| 55 | 0.047 | |
| 56 | 0.014 | |
| 57 | 0.181 | |
| 58 | 0.018 | 0.014 |
| 59 | 0.259 | |
| 62 | 0.086 | |
| 63 | 0.019 | |
| 64 | 0.279 | |
| 65 | 0.057 | |
| 66 | 0.016 | 0.13 |
| 68 | 0.119 | |
| 69 | 0.016 | |
| 70 | 0.224 | |
| 71 | 0.015 | 0.39 |
| 74 | 0.035 | |
| 77 | 0.28 | |
| 78 | 0.080 | |
| 79 | 0.008 | |
| 80 | 0.080 | |
| 81 | 0.017 | |
| 82 | 0.003 | 0.04 |
| 83 | 0.031 | |
| 84 | 0.001 | 0.005 |
| 85 | 0.024 | |
| 86 | 0.047 | |
| 87 | <0.001 | |
| 88 | 0.069 | |
| 89 | 0.005 | 0.30 |
| 90 | 0.055 | |
| 91 | 0.020 | |
| 92 | 0.033 | |
| 93 | 0.010 | 0.05 |
| 94 | 0.038 | |
| 95 | 0.001 | |
| 96 | <0.010 | |
| 97 | 0.015 | |
| 98 | 0.025 | |
| 99 | 0.018 | 0.50 |
| 100 | 0.026 | >1 |
| 101 | 0.008 | >1 |
| 102 | 0.004 | 0.20 |

The following compounds, which are disclosed in U.S. Pat. No. 5,155,110, were also evaluated in the foregoing assays, and each such compound demonstrated little or no inhibitory activity.

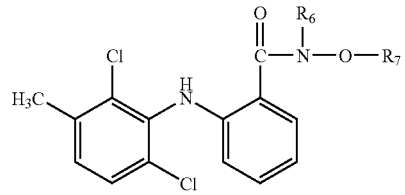

| R$_6$ | R$_7$ | % Inhibition In Vitro |
|---|---|---|
| H | H | 9 at 1 μM |
| | | −3 at 10 μM |
| H | CH$_3$ | −8 at 1 μM |
| | | 8 at 10 μM |
| CH$_3$ | H | −5 at 1 μM |
| | | 19 at 10 μM |
| iPr | H | 17 at 1 μM |
| | | 9 at 10 μM |
| CH$_2$—Ph | H | −4 at 1 μM |
| | | 18 at 10 μM |

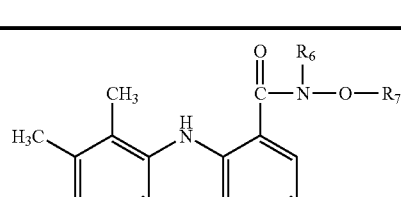

| R$_6$ | R$_7$ | % Inhibition In Vitro |
|---|---|---|
| H | H | 6 at 1 μM |
| | | −4 at 10 μM |
| H | CH$_3$ | −6 at 1 μM |
| | | 12 at 10 μM |
| CH$_3$ | H | 13 at 1 μM |
| | | 19 at 10 μM |
| iPr | H | −11 at 1 μM |
| | | 7 at 10 μM |

EXAMPLE 103

The compound from Example 95, 2-(2-chloro-4-iodophenylamino)-N-cyclopropylmethoxy-3,4-difluorobenzamide, was evaluated in animals implanted with a murine colon tumor, C26/clone 10. Male CD2F1 mice (NCI: Charles River, Kingston) were implanted subcutaneously with tumor fragments (approximately 30 mg) in the region of the right axilla on Day 0. The compound of Example 95 was administered intraperitoneally (IP) or orally (PO) on Days 1 through 14, post-implant, for a total of 14 days (6 mice per group). The vehicle for the test compound, and for control animals, was 10% EtOH/10% Cremophor-EL (Sigma)/80% $H_2O$, pH 5.0. Tumor volumes were recorded three times per week by measuring the length and width of the individual tumors and calculating mass in milligrams according to the formula $(a \times b^2)/2$, where a and b are the length and width of the tumor. Percent treated/control (T/C) was calculated based on the ratio of the median tumor volume of the treated tumors compared with the median tumor volume of control animals on specified measurement days.

In the trial in which the compound of Example 95 was administered IP, the doses were 200, 124, 77, and 48 mg/kg/day. The invention compound inhibited tumor growth by 59% to 100% as assessed on Day 15. The median size of the control tumors on Day 15 was 1594 mg. Table 2 shows the number of animal deaths in each treatment group, the change in body weight, the percent of the median tumor volume of the treated group compared to the control group, and the percent inhibition.

TABLE 2

| Dose | Non-Specific Deaths | Change in Body Weight (grams) | % T/C (Day 15) | % Inhibition |
|---|---|---|---|---|
| 200 | 1/6 | +2 | 0 | 100 |
| 124 | 1/6 | +3 | 4 | 96 |
| 77 | 2/5 | +2 | 2 | 98 |
| 48 | 0/6 | +3 | 41 | 59 |

In the test in which the compound of Example 95 was orally administered, the doses were 300, 186, 115, and 71 mg/kg/day. The invention compound inhibited tumor growth 64% to 83% as assessed on Day 17. The median size of the control tumors on Day 17 was 1664 mg. Table 3 shows the number of animal deaths in each treatment group, the change in body weight, the percent of the median tumor volume of the treated group compared to the control group, and the percent inhibition.

TABLE 3

| Dose | Non-Specific Deaths | Change in Body Weight (grams) | % T/C (Day 17) | % Inhibition |
|---|---|---|---|---|
| 300 | 0/6 | +2 | 17 | 83 |
| 186 | 0/6 | +2 | 25 | 75 |
| 115 | 1/6 | +2 | 21 | 79 |
| 71 | 0/6 | +2 | 36 | 64 |

The foregoing assay established that the invention compounds of Formula I are particularly useful for treating cancers such as colon cancer. The compounds are especially well-suited for use in combination with radiation to treat and control cancers.

The invention compounds will be utilized to treat subjects suffering from cancer and other proliferative diseases and in need of treatment. The compounds are ideally suited to treating psoriasis, restenosis, autoimmune disease, and atherosclerosis. The compounds will generally be utilized as a pharmaceutical formulation, in which the compound of Formula I is present in a concentration of about 5% to about 95% by weight. The compounds can be formulated for convenient oral, parenteral, topical, rectal, or like routes of administration. The compound will be formulated with common diluents, excipients, and carriers routinely utilized in medicine, for instance, with polyols such as glycerin, ethylene glycol, sorbitol 70; mono- and difatty acid esters of ethylene glycol. Starches and sugars such as corn starch, sucrose, lactose, and the like, can be utilized for solid preparations. Such solid formulations can be in the form of tablets, troches, pills, capsules, and the like. Flavoring agents such as peppermint, oil of wintergreen, and the like can be incorporated.

Typical doses of active compound are those that are effective to treat the cancer or other proliferative disorder afflicting the mammal. Doses will generally be from about 0.1 mg per kilogram body weight to about 500 mg per kilogram body weight. Such doses will be administered from one to about four times a day, or as needed to effectively treat the cancer, psoriasis, restenosis, or other proliferative disorder.

A preferred method for delivering the invention compound is orally via a tablet, capsule, solution, or syrup. Another method is parenterally, especially via intravenous infusion of a solution of the benzopyran in isotonic saline or 5% aqueous glucose.

Following are typical formulations provided by the invention.

EXAMPLE 104

Preparation of 50-mg Tablets

| Per Tablet | | Per 10,000 Tablets |
|---|---|---|
| 0.050 g | 4-fluoro-N-hydroxy-2-(4-iodo-2-methyl-phenylamino)-benzamide | 500 g |
| 0.080 g | lactose | 800 g |
| 0.010 g | corn starch (for mix) | 100 g |
| 0.008 g | corn starch (for paste) | 80 g |
| 0.002 g | magnesium stearate (1%) | 20 g |
| 0.150 g | | 1500 g |

The benzhydroxamic acid, lactose, and corn starch (for mix) are blended to uniformity. The corn starch (for paste) is suspended in 600 mL of water and heated with stirring to form a paste. The paste is used to granulate the mixed powders. The granules are passed through a #8 screen and dried at 120° F. The dry granules are passed through a #16 screen. The mixture is lubricated with 1% magnesium stearate and compressed into tablets. The tablets are administered to a mammal for inhibiting MEK enzymes and treating restenosis, atherosclerosis, and psoriasis.

EXAMPLE 105

| Preparation of Oral Suspension | |
|---|---|
| Ingredient | Amount |
| 5-Chloro-2-(4-iodo-2-methyl-phenylamino)-N-(methoxy)-benzamide | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs ad | 100 mL |

The sorbitol solution is added to 40 mL of distilled water and the benzhydroxamic acid derivative is suspended therein. The saccharin, sodium benzoate, flavor, and dye are added and dissolved. The volume is adjusted to 100 mL with distilled water. Each milliliter of syrup contains 5 mg of the invention compound. The syrup is administered to a mammal for treating proliferative disease, especially breast cancer and skin cancer.

EXAMPLE 106

Preparation of Parenteral Solution

In a solution of 700 mL of propylene glycol and 200 mL of water for injection is added 20.0 g of 4-fluoro-2-(4-bromo-2-methyl-phenylamino)-N-(hydroxy)-benzamide. The volume of the solution is adjusted to 1000 mL by addition of water for injection. The formulation is heat sterilized, filled into 50-mL ampoules each containing 2.0 mL (40 mg of 4-fluoro-2-(4-bromo-2-methyl-phenylamino)-N-(hydroxy)-benzamide), and sealed under nitrogen.

The invention compounds thus formulated will be administered to a mammal in need of treatment for a proliferative disorder such as cancer, psoriasis, restenosis, atherosclerosis, and autoimmune disease at a rate and dose effective to treat the condition. An "antiproliferative amount" of an invention compound is that quantity of compound that inhibits or reduces the rate of proliferation of target cells. Typical cancers to be treated according to this invention include breast cancer, colon cancer, prostate cancer, skin cancer, and the like. The compound is well-suited to the treatment of psoriasis, restenosis, and atherosclerosis, and to inhibiting the activity of MEK enzymes, especially $MEK_1$ and $MEK_2$. All that is required is to administer to a mammal an MEK inhibiting amount of a compound of the invention. An "MEK inhibiting amount" of an invention compound is an amount that when administered to a mammal causes a measurable inhibition of the MEK enzyme. Typical MEK inhibiting amounts will be from about 0.1 µg to about 500 mg of active compound per kilogram body weight. For treating the proliferative diseases mentioned above, typical doses will be from about 0.1 to about 50 mg/kg, normally given from one to about four times per day.

What is claimed is:

1. A compound of Formula I

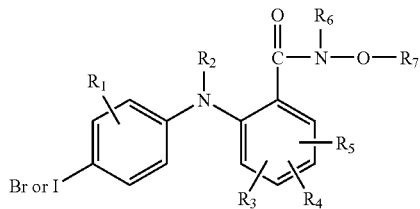

wherein:
$R_1$ is hydrogen, hydroxy, $C_1$–$C_8$ alkyl, $C_1$–$C_8$ alkoxy, halo, trifluoromethyl, or CN;
$R_2$ is hydrogen;
$R_3$, $R_4$, and $R_5$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_9$, where $R_9$ is hydrogen, hydroxy, $CO_2H$ or $NR_{10}R_{11}$;
n is 0 to 4;
m is 0 or 1;
$R_{10}$ and $R_{11}$ independently are hydrogen or $C_1$–$C_8$ alkyl, or taken together with the nitrogen to which they are attached can complete a 3- to 10-member cyclic ring optionally containing one, two, or three additional heteroatoms selected from O, S, NH, or N—$C_1$–$C_8$ alkyl;
$R_6$ is hydrogen, $C_1$–$C_8$ alkyl,

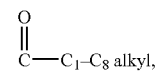

alkyl, aryl, aralkyl, or $C_3$–$C_{10}$ cycloalkyl;
$R_7$ is hydrogen, $C_1$–$C_8$ alkyl, $C_2$–$C_8$ alkenyl, $C_2$–$C_8$ alkynyl;
and wherein any of the foregoing alkyl, alkenyl, and alkynyl groups can be unsubstituted or substituted by cycloalkyl, aryl, aryloxy.

2. The compound according to claim 1 having the formula

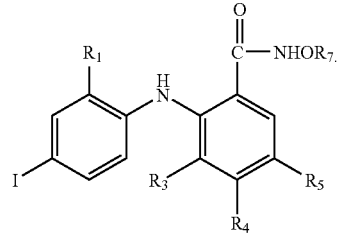

3. The compound of claim 2 wherein $R_1$ is methyl, $R_4$ is fluoro, and $R_3$ and $R_5$ are hydrogen.

4. The compound of claim 3 which is:
4-Fluoro-N-hydroxy-2-(4-iodo-2-methyl-phenylamino)-benzamide;
4-Fluoro-2-(4-iodo-2-methyl-phenylamino)-N-(methoxy)-benzamide;
4-Fluoro-2-(4-iodo-2-methyl-phenylamino)-N-(prop-2-ynyloxy)-benzamide;

4-Fluoro-2-(4-iodo-2-methyl-phenylamino)-N-(2-phenoxyethoxy)-benzamide;
4-Fluoro-2-(4-iodo-2-methyl-phenylamino)-N-(prop-2-enyloxy)-benzamide; or
4-Fluoro-2-(4-iodo-2-methyl-phenylamino)-N-(cyclopropylmethoxy)-benzamide.

5. The compound of claim 2 wherein $R_1$ is methyl or chloro, $R_3$ and $R_4$ are fluoro, and $R_5$ is hydrogen.

6. The compound of claim 5 which is:
3,4-Difluoro-2-(4-iodo-2-methyl-phenylamino)-N-ethoxy-benzamide;
3,4-Difluoro-2-(4-iodo-2-methyl-phenylamino)-N-(but-2-enyloxy)-benzamide;
3,4-Difluoro-2-(4-iodo-2-methyl-phenylamino)-N-(cyclopropylmethoxy)-benzamide;
3,4-Difluoro-2-(4-iodo-2-methyl-phenylamino)-N-(1-methylprop-2-ynyloxy)-benzamide;
3,4-Difluoro-2-(4-iodo-2-methyl-phenylamino)-N-(3-phenylprop-2-ynyloxy)-benzamide;
3,4-Difluoro-2-(4-iodo-2-methyl-phenylamino)-N-(3-methyl-5-phenylpent-2-en-4-ynyloxy)-benzamide;
3,4-Difluoro-2-(4-iodo-2-methyl-phenylamino)-N-(prop-2-ynyloxy)-benzamide;
3,4-Difluoro-2-(4-iodo-2-methyl-phenylamino)-N-(propoxy)-benzamide;
3,4-Difluoro-2-(4-iodo-2-methyl-phenylamino)-N-(2-methyl-prop-2-enyloxy)-benzamide;
3,4-Difluoro-2-(4-iodo-2-methyl-phenylamino)-N-(2-phenoxyethoxy)-benzamide;
3,4-Difluoro-2-(4-iodo-2-methyl-phenylamino)-N-(but-2-enyloxy)-benzamide;
3,4-Difluoro-2-(4-iodo-2-methyl-phenylamino)-N-(but-3-ynyloxy)-benzamide;
3,4-Difluoro-2-(4-iodo-2-methyl-phenylamino)-N-(3-(2-fluorophenyl)-prop-2-ynyloxy)-benzamide;
3,4-Difluoro-N-hydroxy-2-(4-iodo-2-methyl-phenylamino)-benzamide;
3,4-Difluoro-2-(2-chloro-4-iodo-phenylamino)-N-cyclobutylmethoxy-benzamide;
3,4-Difluoro-2-(2-chloro-4-iodo-phenylamino)-N-cyclopropylmethoxy-benzamide.

7. A compound which is 3,4-difluoro-2-(2-chloro-4-iodo-phenylamino)-N-cyclopropylmethoxy-benzamide.

8. The compound of claim 2 wherein $R_1$ is methyl or chloro, $R_3$ and $R_4$ are fluoro, and $R_5$ is bromo.

9. The compound according to claim 8 which is:
5-Bromo-3,4-difluoro-N-hydroxy-2-(4-iodo-2-methyl-phenylamino)-benzamide;
5-Bromo-3,4-difluoro-2-(4-iodo-2-methyl-phenylamino)-N-(n-propoxy)-benzamide;
5-Bromo-N-(but-2-enyloxy)-3,4-difluoro-2-(4-iodo-2-methyl-phenylamino)-benzamide
5-Bromo-N-butoxy-3,4-difluoro-2-(4-iodo-2-methyl-phenylamino)-benzamide;
5-Bromo-3,4-difluoro-2-(4-iodo-2-methyl-phenylamino)-N-(3-methyl-but-2-enyloxy)-benzamide;
5-Bromo-3,4-difluoro-2-(4-iodo-2-methyl-phenylamino)-N-(3-methyl-pent-2-en-4-ynyloxy)-benza
5-Bromo-3,4-difluoro-2-(4-iodo-2-methyl-benzyl)-N-[5-(3-methoxy-phenyl)-3-methyl-pent-2-en-4-ynyloxy]-benzamide;
5-Bromo-3,4-difluoro-2-(4-iodo-2-methyl-phenylamino)-N-(prop-2-ynyloxy)-benzamide;
5-Bromo-3,4-difluoro-2-(4-iodo-2-methyl-phenylamino)-N-[3-(3-methoxy-phenyl)-prop-2-ynyloxy]-benzamide;
5-Bromo-3,4-difluoro-2-(4-iodo-2-methyl-phenylamino)-N-(pyridin-3-ylmethoxy)-benzamide;
5-Bromo-3-4-difluoro-2-(4-iodo-2-methyl-phenylamino)-N-(3-(2-fluorophenyl)-prop-2-ynyloxy)-benzamide;
5-Bromo-3,4-difluoro-2-(4-iodo-2-methyl-phenylamino)-N-(ethoxy)-benzamide;
5-Bromo-3,4-difluoro-2-(4-iodo-2-methyl-phenylamino)-N-(cyclopropylmethoxy)-benzamide;
5-Bromo-3,4-difluoro-2-(4-iodo-2-methyl-phenylamino)-N-(isopropoxy)-benzamide;
5-Bromo-3,4-difluoro-2-(4-iodo-2-methyl-phenylamino)-N-but-3-ynyloxy)-benzamide;
5-Bromo-N-(2-diethylamino-ethoxy)-3,4-difluoro-(4-iodo-2-methyl-phenylamino)-benzamide;
5-Bromo-3,4-difluoro-2-(4-iodo-2-methyl-phenylamino)-N-isobutoxy-benzamide;
5-Bromo-N-cyclohexylmethoxy-3,4-difluoro-2-(4-iodo-2-methyl-phenylamino)-benzamide;
5-Bromo-N-cyclopentylmethoxy-3,4-difluoro-2-(4-iodo-2-methyl-phenylamino)-benzamide;
5-Bromo-N-cyclobutylmethoxy-3,4-difluoro-2-(4-iodo-2-methyl-phenylamino)-benzamide;
5-Bromo-2-(2-chloro-4-iodo-phenylamino)-N-(2-dimethylamino-ethoxy)-3,4-difluoro-benzamide monohydrochloride salt;
5-Bromo-N-(2-dimethylamino-propoxy)-3,4-difluoro-2-(4-iodo-2-methyl-phenylamino)-benzamide;
5-Bromo-2-(2-chloro-4-iodo-phenylamino)-3,4-difluoro-N-hydroxy-benzamide; or
5-Bromo-2-(2-chloro-4-iodo-phenylamino)-N-cyclopropylmethoxy-3,4-difluoro-benzamide.

10. The compound of claim 2 wherein $R_1$ is methyl, $R_3$ and $R_4$ are hydrogen, and $R_5$ is halo.

11. The compound according to claim 10 which is:
5-Chloro-N-hydroxy-2-(4-iodo-2-methyl-phenylamino)-benzamide;
5-Chloro-2-(4-iodo-2-methyl-phenylamino)-N-methoxy-benzamide;
4-Bromo-2-(4-iodo-2-methyl-phenylamino)-N-phenylmethoxy-benzamide;
4-Fluoro-2-(4-iodo-2-methyl-phenylamino)-N-phenylmethoxy-benzamide;
5-Fluoro-N-hydroxy-2-(4-iodo-2-methyl-phenylamino)-benzamide; or
5-Iodo-2-(4-iodo-2-methyl-phenylamino)-N-phenylmethoxy-benzamide.

12. The compound of claim 2 having the formula

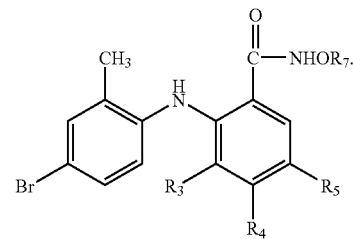

wherein $R_3$ and $R_4$ are fluoro, and $R_5$ is hydrogen.

13. The compound according to claim 12 which is:
3,4-Difluoro-2-(4-bromo-2-methyl-phenylamino)-N-(3-phenylprop-2-ynyloxy)-benzamide;
3,4-Difluoro-2-(4-bromo-2-methyl-phenylamino)-N-(but-3-ynyloxy)-benzamide;

3,4-Difluoro-2-(4-bromo-2-methyl-phenylamino)-N-(2-methyl-prop-2-enyloxy)-benzamide;
3,4-Difluoro-2-(4-bromo-2-methyl-phenylamino)-N-(but-2-enyloxy)-benzamide;
3,4-Difluoro-2-(4-bromo-2-methyl-phenylamino)-N-(methoxy)-benzamide;
3,4-Difluoro-2-(4-bromo-2-methyl-phenylamino)-N-(ethoxy)-benzamide;
3,4-Difluoro-2-(4-bromo-2-methyl-phenylamino)-N-(isopropoxy)-benzamide;
3,4-Difluoro-2-(4-bromo-2-methyl-phenylamino)-N-(2-phenoxyethoxy)-benzamide;
3,4-Difluoro-2-(4-bromo-2-methyl-phenylamino)-N-(cyclopropylmethoxy)-benzamide;
3,4-Difluoro-2-(4-bromo-2-methyl-phenylamino)-N-(n-propoxy)-benzamide;
3,4-Difluoro-2-(4-bromo-2-methyl-phenylamino)-N-(1-methyl-prop-2-ynyloxy)-benzamide;
3,4-Difluoro-2-(4-bromo-2-methyl-phenylamino)-N-(3-(3-fluorophenyl)-prop-2-ynyloxy)-benzamide;
3,4-Difluoro-2-(4-bromo-2-methyl-phenylamino)-N-(4,4-dimethylpent-2-ynyloxy)-benzamide; and
3,4-Difluoro-2-(4-bromo-2-methyl-phenylamino)-N-(cyclopentoxy)-benzamide.

14. The compound according to claim 1 which is:
3,4,5-Trifluoro-N-hydroxy-2-(4-iodo-2-methyl-phenylamino)-benzamide;
5-Chloro-3,4-difluoro-N-hydroxy-2-(4-iodo-2-methyl-phenylamino)-benzamide;
5-Bromo-3,4-difluoro-2-(2-fluoro-4-iodo-phenylamino)-N-hydroxy-benzamide;
N-Hydroxy-2-(4-iodo-2-methyl-phenylamino)-4-nitro-benzamide;
3,4,5-Trifluoro-2-(2-fluoro-4-iodo-phenylamino)-N-hydroxy-benzamide;
5-Chloro-3,4-difluoro-2-(2-fluoro-4-iodo-phenylamino)-N-hydroxy-benzamide;
5-Bromo-2-(2-chloro-4-iodo-phenylamino)-3,4-difluoro-N-hydroxy-benzamide;
2-(2-Fluoro-4-iodo-phenylamino)-N-hydroxy-4-nitro-benzamide;
2-(2-Chloro-4-iodo-phenylamino)-3,4,5-trifluoro-N-hydroxy-benzamide;
4-Fluoro-N-hydroxy-2-(4-iodo-2-methyl-phenylamino)-5-nitro-benzamide;
2-(2-Chloro-4-iodo-phenylamino)-N-hydroxy-4-nitro-benzamide;
5-Chloro-2-(2-chloro-4-iodo-phenylamino)-3,4-difluoro-N-hydroxy-benzamide;
5-Bromo-2-(2-bromo-4-iodo-phenylamino)-3,4-difluoro-N-hydroxy-benzamide;
2-(2-Chloro-4-iodo-phenylamino)-N-hydroxy-4-methyl-benzamide;
2-(2-Bromo-4-iodo-phenylamino)-3,4,5-trifluoro-N-hydroxy-benzamide;
2-(2-Bromo-4-iodo-phenylamino)-5-chloro-3,4-difluoro-N-hydroxy-benzamide;
2-(2-Bromo-4-iodo-phenylamino)-N-hydroxy-4-nitro-benzamide;
4-Fluoro-2-(2-fluoro-4-iodo-phenylamino)-N-hydroxy-benzamide;
3,4-Difluoro-2-(2-fluoro-4-iodo-phenylamino)-N-hydroxy-benzamide;
2-(2-Chloro-4-iodo-phenylamino)-4-fluoro-N-hydroxy-benzamide;
2-(2-Chloro-4-iodo-phenylamino)-3,4-difluoro-N-hydroxy-benzamide;
2-(2-Bromo-4-iodo-phenylamino)-4-fluoro-N-hydroxy-benzamide;
2-(2-Bromo-4-iodo-phenylamino)-3,4-difluoro-N-hydroxy-benzamide;
N-Cyclopropylmethoxy-3,4,5-trifluoro-2-(4-iodo-2-methyl-phenylamino)-benzamide;
5-Chloro-N-cyclopropylmethoxy-3,4-difluoro-2-(4-iodo-2-methyl-phenylamino)-benzamide;
5-Bromo-N-cyclopropylmethoxy-3,4-difluoro-2-(2-fluoro-4-iodo-phenylamino)-benzamide;
N-Cyclopropylmethoxy-2-(4-iodo-2-methyl-phenylamino)-4-nitro-benzamide;
N-Cyclopropylmethoxy-3,4,5-trifluoro-2-(2-fluoro-4-iodo-phenylamino)-benzamide;
5-Chloro-N-cyclopropylmethoxy-3,4-difluoro-2-(2-fluoro-4-iodo-phenylamino)-benzamide;
5-Bromo-2-(2-chloro-4-iodo-phenylamino)-N-cyclopropylmethoxy-3,4-difluoro-benzamide;
N-Cyclopropylmethoxy-2-(2-fluoro-4-iodo-phenylamino)-4-nitro-benzamide;
2-(2-Chloro-4-iodo-phenylamino)-N-cyclopropylmethoxy-3,4,5-trifluoro-benzamide;
5-Chloro-2-(2-chloro-4-iodo-phenylamino)-N-cyclopropylmethoxy-3,4-difluoro-benzamide;
5-Bromo-2-(2-bromo-4-iodo-phenylamino)-N-ethoxy-3,4-difluoro-benzamide;
2-(2-Chloro-4-iodo-phenylamino)-N-ethoxy-4-nitro-benzamide;
2-(2-Bromo-4-iodo-phenylamino)-N-cyclopropylmethoxy-3,4,5-trifluoro-benzamide;
2-(2-Bromo-4-iodo-phenylamino)-5-chloro-N-cyclopropylmethoxy-3,4-difluoro-benzamide
2-(2-Bromo-4-iodo-phenylamino)-N-cyclopropylmethoxy-4-nitro-benzamide;
N-Cyclopropylmethoxy-4-fluoro-2-(2-fluoro-4-iodo-phenylamino)-benzamide;
N-Cyclopropylmethoxy-3,4-difluoro-2-(2-fluoro-4-iodo-phenylamino)-benzamide;
2-(2-Chloro-4-iodo-phenylamino)-N-cyclopropylmethoxy-4-fluoro-benzamide;
2-(2-Chloro-4-iodo-phenylamino)-N-cyclopropylmethoxy-3,4-difluoro-benzamide;
2-(2-Bromo-4-iodo-phenylamino)-N-cyclopropylmethoxy-4-fluoro-benzamide;
2-(2-Bromo-4-iodo-phenylamino)-N-cyclopropylmethoxy-3,4-difluoro-benzamide;
N-Cyclopropylmethoxy-3,4,5-trifluoro-2-(4-iodo-2-methyl-phenylamino)-benzamide;
4-Fluoro-N-hydroxy-2-(4-iodo-2-methyl-phenylamino)-5-nitro-benzamide;
2-(2-Chloro-4-iodo-phenylamino)-N-hydroxy-4-nitro-benzamide;
3,4-Difluoro-N-hydroxy-2-(4-iodo-2-methyl-phenylamino)-benzamide;
2-(2-Chloro-4-iodo-phenylamino)-4-fluoro-N-hydroxy-benzamide (HCl salt);
2-(2-Chloro-4-iodo-phenylamino)-N-cyclobutylmethoxy-3,4-difluoro-benzamide;
5-Bromo-2-(2-chloro-4-iodo-phenylamino)-N-(2-dimethylamino-ethoxy)-3,4-difluoro-benzamide monohydrochloride salt;
5-Bromo-N-(2-dimethylamino-propoxy)-3,4-difluoro-2-(4-iodo-2-methyl-phenylamino)-benzamide;
5-Bromo-2-(2-chloro-4-iodo-phenylamino)-3,4-difluoro-N-hydroxy-benzamide;
2-(2-Chloro-4-iodo-phenylamino)-N-cyclopropylmethoxy-3,4-difluoro-benzamide; or 5-Bromo-2-(2-chloro-4-iodo-phenylamino)-N-cyclopropylmethoxy-3,4-difluoro-benzamide.

15. A pharmaceutical formulation comprising a compound of claim 1 admixed with a pharmaceutically acceptable excipient, diluent, or carrier.

16. A pharmaceutical formulation comprising a compound of claim 7 admixed with a pharmaceutically acceptable excipient, diluent, or carrier.

* * * * *